United States Patent [19]
Druliner et al.

[11] Patent Number: 6,160,183
[45] Date of Patent: Dec. 12, 2000

[54] DIRECT OXIDATION OF CYCLOALKANES

[75] Inventors: Joe Douglas Druliner; Norman Herron, both of Newark, Del.; Kostantinos Kourtakis, Swedesboro, N.J.

[73] Assignee: E. I. du Pont de Nemours and Company, Wilmington, Del.

[21] Appl. No.: 09/245,754

[22] Filed: Feb. 8, 1999

Related U.S. Application Data

[60] Provisional application No. 60/074,259, Feb. 10, 1998.

[51] Int. Cl.$^7$ .................................................. C07C 45/33
[52] U.S. Cl. ...................... 568/360; 568/401; 568/835; 568/836
[58] Field of Search ..................... 568/311, 342, 568/385, 835, 836, 909.8, 360, 401

[56] References Cited

U.S. PATENT DOCUMENTS

| | | | |
|---|---|---|---|
| 3,530,185 | 9/1970 | Pugi et al. | 260/586 |
| 3,987,101 | 10/1976 | Wolters et al. | 260/586 R |
| 4,042,630 | 8/1977 | Wolters et al. | 260/586 R |
| 4,326,084 | 4/1982 | Druliner et al. | 568/360 |
| 5,004,837 | 4/1991 | Baur et al. | 568/342 |
| 5,298,665 | 3/1994 | Janssen et al. | 568/342 |
| 5,932,750 | 8/1999 | Hayashi et al. | 549/523 |

FOREIGN PATENT DOCUMENTS

| | | | |
|---|---|---|---|
| 0709.360 | 12/1998 | European Pat. Off. | 45/33 |
| WO92/16487 | 10/1992 | WIPO . | |
| WO98/34894 | 8/1998 | WIPO . | |

*Primary Examiner*—Sreeni Padmanabhan

[57] ABSTRACT

A catalytic process is disclosed for oxidizing cycloalkanes directly to form, in a single step, a mixture containing the corresponding alcohol and ketone. In particular, the invention relates to oxidizing a cycloalkane by contacting it with a source of oxygen and a catalytic amount of a heterogeneous catalyst. The catalysts of the invention include gold (including gold sol-gel compounds) and sol-gel compounds containing particular combinations of Cr, Co, Zr, Ta, Si, Mg, Nb, Al and Ti, wherein certain of those metals have been combined with an oxide, such as an inorganic matrix of hydroxides or oxides, or combinations thereof. The catalysts may also optionally be supported on a suitable support member.

17 Claims, No Drawings

DIRECT OXIDATION OF CYCLOALKANES

This application claim benefit to Provisional application No. 60/074,259 filing date Feb. 10, 1998.

FIELD OF INVENTION

The invention generally relates to an improved catalytic process for oxidizing cycloalkanes to form a mixture containing the corresponding alcohol and ketone. In particular, the invention relates to directly oxidizing cyclohexane to form a mixture containing cyclohexanol and cyclohexanone by contacting cyclohexane with an oxygen source and a catalytic amount of a heterogenous catalyst of gold or a sol-gel compound containing particular combinations of Cr, Co, Zr, Ta, Si, Ti, Nb, Al and Mg, wherein certain of those metals have been combined with an oxide.

BACKGROUND OF THE INVENTION

Industrial processes for the production of mixtures of cyclohexanol and cyclohexanone from cyclohexane are currently of considerable commercial significance and are described in the patent literature. In typical industrial practice, cyclohexane is oxidized to form a reaction mixture containing cyclohexyl hydroperoxide (CHHP). The resulting CHHP is decomposed, optionally in the presence of a catalyst, to form a reaction mixture containing cyclohexanol and cyclohexanone. In the industry, such a mixture is known as a K/A (ketone/alcohol) mixture, and can be readily oxidized to produce adipic acid, which is an important reactant in processes for preparing certain condensation polymers, notably polyamides. Due to the large volumes of adipic acid consumed in these and other processes, improvements in processes for producing adipic acid and its precursors can be used to provide beneficial cost advantages.

A representative example of the oxidation of cyclohexane to CHHP can be found in Druliner et al., U.S. Pat. No. 4,326,084, in which cobalt salts are used as homogenous catalysts to form a reaction mixture containing CHHP, and for subsequently decomposing the resulting CHHP to form a mixture containing K and A.

Druliner et al., WO98/34894, Aug. 4, 1998, disclose decomposing a hydroperoxide by contacting it with a catalytic amount of a heterogeneous catalyst selected from the group consisting of Au (gold), Ag (silver), and Cu (copper). Preferably, the catalyst is supported on a solid support such as $SiO_2$, $Al_2O_3$, carbon, MgO or $TiO_2$.

Komiya et al., (J. Molecular Catalysis A, 117, p 21–37, 1997) studied the oxidation of alkanes to the corresponding alcohols and ketones using molecular oxygen and copper catalysts. However, the presence of stoichiometric amounts of aldehydes is required in order to form a peracid intermediate which functions as the actual oxidizing reagent.

Pugi, K. (U.S. Pat. No. 3,530,185) teaches a process for the oxidation of cyclohexane to K and A, optionally using a soluble cobalt catalyst. However, the resulting mixture contains significant amounts of CHHP.

In view of the above, it would be desirable to have catalysts that would produce K and A directly from cyclohexane without the additional CHHP decomposition step which would result in simpler processing and less loss of product. The use of the most desirable catalysts would result in high conversion and selectivity along with little or no CHHP or high oxidation products present in the final product.

It is thus an object of the present invention to overcome some of the deficiencies of the prior art and further to provide a process for the one-step oxidation of cycloalkanes (cyclohexane) to the corresponding alcohol (cyclohexanol) and ketone (cyclohexanone) using a heterogeneous catalyst that results in little or no CHHP present in the final product mixture. Other objects and advantages of the present invention will become apparent to those skilled in the art upon reference to the detailed description which follows hereinafter.

SUMMARY OF THE INVENTION

In accordance with the present invention, an improved process is provided for oxidizing a cycloalkane (preferably cyclohexane) to form a reaction mixture containing a corresponding alcohol (A) and ketone (K), the improvement comprising oxidizing a cycloalkane by contacting the cycloalkane with a source of oxygen and a catalytic amount of a heterogenous catalyst selected from the group consisting of (1) gold and (2) a sol-gel compound comprised of (a) one or more members selected from a first group consisting of Cr, Co and Ti and (b) one or more members selected from a second group consisting of Zr, Nb, Ta, Si, Al, Mg and Ti, wherein the selected members of (b) are combined with an oxide and wherein members of the first group cannot be the same as members of the second group. Preferably, an inorganic matrix of hydroxides or oxides, or combinations thereof, is used as the oxide.

The catalysts are optionally supported on a catalyst solid support member. An initiator, preferably propionaldehyde, is also optionally present with the catalyst. Particularly preferred catalysts include gold supported on $Al_2O_3$ and sol-gel compounds containing Au, Cr and/or Co.

DETAILED DESCRIPTION OF THE PREFERRED EMBODIMENTS

In accordance with the present invention, cycloalkanes may be directly oxidized in the presence of an oxygen source and a catalyst to yield the corresponding alcohol and ketone with little or no corresponding hydroperoxide present in the final product.

The heterogenous catalysts of the invention include Au (including, but not limited to, sol-gel compounds of gold), preferably applied to a suitable solid support, and sol-gel compounds comprised of (a) one or more of Cr, Co and Ti and (b) one or more of Zr, Ta, Nb, Si, Al, Mg and Ti that are combined with an oxide, but where there are at least two different metals present in the compound. For the supported Au catalyst, the metal to support percentage can vary from about 0.01 to about 50 percent by weight, and is preferably about 0.1 to about 10 wt. percent. Suitable supports include $SiO_2$ (silica), $Al_2O_3$ (alumina), $ZrO_2$ (zirconia), C (carbon) and $TiO_2$ (titania). Alumina is a preferred support, and Au supported on alumina is a particularly preferred catalyst of the invention.

The inventive process can also be carried out using Au, Ag, or Cu in the presence of other metals such as Pd. Preferably, the metals added to the heterogeneous catalysts of the invention are for use as promoters, synergistic additives, or co-catalysts and are selected from Group VIII metals such as Fe, Co, Ni, Ru, Rh, Pd, Os, Ir, and Pt. The term "Group VIII" refers to the CAS version of the Periodic Table of the Elements, CRC Handbook of Physics and Chemistry, $67^{th}$ edition, CRC Press, Boca Raton, Fla.

Some of the heterogenous catalysts of the invention can be obtained already prepared from manufacturers, or they can be prepared from suitable starting materials using methods known in the art. These methods can include sol-gel techniques as described in more detail below for preparing both gold and other non-gold sol-gel compounds. Supported gold catalysts can be prepared by any standard procedure known to give well-dispersed gold, such as evaporative techniques or coatings from colloidal dispersions.

In particular, ultra-fine particle sized gold is preferred. Such small particulate gold (often smaller than 10 nm) can be prepared according to Haruta, M., "Size-and Support-Dependency in the Catalysis of Gold", Catalysis Today 36 (1997) 153–166 and Tsubota et al., Preparation of Catalysts V, pp. 695–704 (1991). Such gold preparations produce samples that are purple-pink in color instead of the typical bronze color associated with gold and result in highly dispersed gold catalysts when placed on a suitable support member. These highly dispersed gold particles typically are from about 3 nm to about 15 nm in diameter.

The catalyst solid support member, including $SiO_2$, $Al_2O_3$, $ZrO_2$, carbon, or $TiO_2$, can be amorphous or crystalline, or a mixture of amorphous and crystalline forms. Selection of an optimal average particle size for the catalyst supports will depend upon such process parameters as reactor residence time and desired reactor flow rates. Generally, the average particle size of the support selected will vary from about 0.005 mm to about 5 mm. Catalysts having a surface area larger than 10 $m^2/g$ are preferred since increased surface area of the catalyst has a direct correlation with increased reaction rates in batch experiments. Supports having much larger surface areas can also be employed, but inherent brittleness of high-surface area catalysts, and attendant problems in maintaining an acceptable particle size distribution, will establish a practical upper limit upon catalyst support surface area.

Other catalysts useful in the present invention are comprised of certain metals (including metal ions) combined with an oxide, such as an inorganic matrix of hydroxides or oxides, or combinations thereof. The metals include Cr, Co, Zr, Ta, Nb, Al, Si, Ti and Mg, present in combinations as set forth before. The mole percentage of metals in the matrix can vary, as can the number of different metals and their relative ratios. They also may have variable hydroxide content, which can depend on calcination temperature, if performed, and other parameters. The transition metals Co and Cr can be present as inorganic salts while Zr, Ta, Nb, Si, Al, Ti and Mg can be present as an oxide, a hydroxide or combinations thereof. (Note that for simplification the corresponding anions are not shown for these cations in the formulae identified herein). Typical preparations involve sol-gel chemistry wherein the metals are co-hydrolyzed and/or entrapped within an inorganic matrix. Better dispersion and uniformity of the metal can be obtained compared to that normally attainable using more conventional synthetic methods. The inorganic matrix can optionally be supported on an appropriate support member, such as $SiO_2$, $Al_2O_3$, $ZrO_2$, carbon, or $TiO_2$. Preferred catalysts of this type are those containing Cr and/or Co.

A "sol-gel technique" is a process wherein a free flowing fluid solution, "sol", is first prepared by dissolving suitable precursor materials such as colloids, alkoxides or metal salts in a solvent. The "sol" is then dosed with a reagent to initiate reactive polymerization of the precursor. A typical example is tetraethoxyorthosilicate (TEOS) dissolved in ethanol. Water, with trace acid or base as catalyst to initiate hydrolysis, is added. As polymerization and crosslinking proceeds, the free flowing "sol" increases in viscosity and can eventually set to a rigid "gel". The "gel" consists of a crosslinked network of the desired material which encapsulates the original solvent within its open porous structure. The "gel" may then be dried, typically by either simple heating in a flow of dry air to produce a xerogel or the entrapped solvent may be removed by displacement with a supercritical fluid such as liquid $CO_2$ to produce an aerogel. These aerogels and xerogels may be optionally calcined at elevated temperatures (>200° C.) which results in products which typically have very porous structures and concomitantly high surface areas.

In practice of the invention, the catalysts can be contacted with a cycloalkane, such as cyclohexane, by formulation into a catalyst bed, which is arranged to provide intimate contact between the catalyst and reactants. Alternatively, catalysts can be slurried with reaction mixtures using techniques known in the art. The process of the invention is suitable for batch or for continuous cycloalkane oxidation processes. These processes can be performed under a wide variety of conditions.

Suitable reaction temperatures for the process of the invention range from about 160° C. to about 200° C. Temperatures from about 160° C. to about 180° C. are typically preferred. Reaction pressures can preferably range from about 69 kPa to about 2760 kPa (10–400 psi) pressure, and pressures from about 276 kPa to about 1380 kPa (40–200 psi) are more preferred. Reaction time varies in inverse relation to reaction temperature, and typically ranges from about 2 to about 30 minutes.

The reaction process can optionally contain an initiator, preferably a 2–6 carbon aliphatic aldehyde. The most preferred is propionaldehyde.

The source of oxygen used in the oxidation may be molecular oxygen itself but is conveniently air or other mixtures of nitrogen and oxygen with a higher or lower proportion of oxygen than that of air, obtained, for example, by mixing oxygen or nitrogen with air. However, air is preferred.

The following non-limiting Examples are provided to further illustrate and enable the invention but are not intended to limit it in any way.

MATERIALS AND METHODS

Experiment 1

~1% Au on γ-alumina

According to the general gold deposition technique of Tsubota et al., Preparation of Catalysts V, pp. 695–704 (1991) to produce ultra-fine gold particles, 10 g of powdered—60 mesh γ-alumina (Alfa Aesar, Ward Hill, Mass.) was slurried into a solution of 0.2 g gold trichloride in 50 mL water containing 1 mL concentrated HCl. The pH of the slurry was adjusted to 9.6 with sodium carbonate solution and then 0.69 g sodium citrate was added. After stirring for 2 hours at room temperature the solid was recovered by filtration and washed well with distilled water. The recovered solid was calcined in flowing air (100 mL/min.) at 250° C. for 5 hours, cooled and then stored in tightly capped vial for testing as a cyclohexane oxidation catalyst. The resulting catalyst was purple/pink in color and had a particle size of 8 nm as determined by x-ray diffraction (XRD).

Experiment 2

CrZrO $Cr_{0.05}(ZrO_{2-x}(OH)_{2x})_{0.95}$ 218 mL of ethanol (Quantum Chemical, Newark, N.J., dehydrated punctilious) was combined with 93.4 g of zirconium n-propoxide (70 wt % in n-propanol, Alfa 22989, Ward Hill, Mass.) in an inert atmosphere $N_2$ drybox. 5.24 g of chromium (III) acetylacetonate (Aldrich, 20, 223-2, Ward Hill Mass.) was dissolved in 218 mL of ethanol and was added to this solution. In a separate container, 218 mL of ethanol was mixed with 20.5 mL of water and 2.45 mL of glacial acetic acid (J. T. Baker, 6903-05, Phillipsburg, N.J.) and 1.91 mL of 70 wt % nitric acid (EM Sciences, Gibbstown N.J.).

The aqueous solution was added, in a dropwise fashion, to the zirconium alkoxide solution. The experiment was performed in a resin kettle under a blanket of flowing nitrogen during the addition of the aqueous solution. During hydrolysis, and prior to the observation of a gel point, some opaqueness and possible white particle formation was noted in the zirconium alkoxide solution. The opaque gel material was allowed to age at room temperature for at least 24 hours.

The material was dried at 120° C. in 1 atmosphere air prior to use. For some experiments, the material was pressed at 20,000 psi into small disks and granulated to sieve through −10, +20 mesh screens.

Experiment 2a

CrZrO (extracted)

$$Cr_{0.05} (ZrO_{2-x}(OH)_{2x})_{0.95}$$

The compounds were made as in Experiment 2 but in place of air drying they were extracted using supercritical $CO_2$. The solvent removal was accomplished by placing the material in a stirred autoclave. $CO_2$ gas was purged over the catalyst for a period of 7 hours, at 40° C. and a pressure of 3500 psi. The xerogel produced following this exposure was a free flowing powder.

Experiment 3

CrTaO $$Cr_{0.05} (TaO_{2.5-x}(OH)_{2x})_{0.95}$$

350 mL of ethanol (Quantum Chemical, Newark, N.J., dehydrated punctilious) was combined with 115.8 g of tantalum ethoxide $(Ta(OEt)_5$, Aldrich, 33, 91103, Milwaukee, Wis.) in an inert atmosphere $N_2$ drybox. 5.24 g of chromium (III) acetylacetonate (Aldrich, 20, 223-2, Ward Hill Mass.) was dissolved in 350 mL ethanol added to the alkoxide solution. In a separate container, 350 mL of ethanol was mixed with 25.7 mL of water and 3.06 mL of glacial acetic acid (J. T. Baker, 6903-05, Phillipsburg, N.J.) and 2.39 mL of 70 wt % nitric acid (EM Sciences, Gibbstown N.J.).

The aqueous solution was added, in a dropwise fashion, to the tantalum alkoxide solution containing soluble chromium acetylacetonate. The material was contained in a resin kettle and was placed under a blanket of flowing nitrogen during this addition. Following hydrolysis, a clear, dark purple gel formed. A clear gel point was observed after approximately seven days at room temperature under flowing nitrogen.

The material was dried at 120° C. in 1 atmosphere air prior to use. For some experiments, the material was pressed at 20,000 psi into small disks and granulated to sieve through −10, +20 mesh screens.

Experiment 3a

CrTaO (extracted)

$$Cr_{0.05} (TaO_{2.5-x}(OH)_{2x})_{0.95}$$

The compounds were made as in Experiment 3, but were further extracted by the same procedure described in Experiment 2a.

Experiment 4

CrTiO $$Cr_{0.2} (TiO_{2-x}(OH)_{2x})_{0.8}$$

13.85 mL of 60 volume % solution in ethanol containing titanium n-butoxide [Aldrich, 24-411-2] in ethanol was added to 50.08 mL of ethanol under an inert nitrogen atmosphere. 6.06 mL of a separate 1.5 molar (metals content) aqueous solution of 1.5 molar chromium hydroxide acetate [Aldrich, 31, 810-8] was slowly added to the alcohol solution, with gentle swirling, to form the green colloidal gel. The material was dried at 120° C. in air prior to use.

Experiment 5

CoCrTiO $$Co_{0.2} Cr_{0.2} (TiO_{2-x}(OH)_{2-x})$$

14.57 mL of a 60 volume % solution in ethanol containing titanium n-butoxide [Aldrich, 24-411-2] was added to 52.68 mL of ethanol. 8.50 mL of an aqueous 1.5 molar solution of chromium hydroxide acetate [Aldrich, 31, 810-8] and 12.75 mL of a 1.0 M aqueous solution of cobalt chloride [Alfa, 12303], were added to the alkoxide solution. During the addition, the glass container was gently swirled under an inert nitrogen atmosphere. The gelled material was dried at 120° C. in air prior to use.

Experiment 6

TiSiO $$Ti_{0.1} Si_{0.9} (O_{2-x}(OH)_{2x})$$

1.915 mL of a tetraethylorthosilicate (Aldrich, 13, 190-3) solution containing 60 volume % alkoxide in ethanol was added to 26.43 mL of titanium n-butoxide (Aldrich, 24, 411-2) solution, also containing 60 volume % of the alkoxide in ethanol. 67.43 mL of ethanol was added to form a mixed alkoxide solution. The solution was kept under a nitrogen atmosphere.

A solution containing 3.712 mL of water mixed with 0.515 mL of glacial acetic acid (EM Sciences, X0409PS-1) was added to the alkoxide solution. During the addition of the aqueous components, the glass container was gently swirled under an inert nitrogen atmosphere. A gelatinous white gel formed almost immediately on addition and allowed to age at room temperature for at least 24 hours. The gelled material was dried at 120° C. in air prior to use.

Experiment 7

CoSiTiO $$Co_{0.5} Ti_{0.4} Si_{0.1} (O_{2-x}(OH)_{2x})_{0.5}$$

3.86 mL of 60 volume % TEOS, 23.661 mL of 60 volume % titanium n-butoxide, and 16.45 mL of ethanol were used to form the alkoxide solution. To this solution, 3.74 mL of $H_2O$, 0.425 mL of glacial acetic acid, and 51.879 mL of a 1.0 M solution of cobalt (II) chloride (Alfa, 12303) in ethanol were added while gently swirling the glass container. A blanket of nitrogen gas was used throughout. A blue red gelatinous material was produced. After aging 24 hours in air, the material was dried at 120° C. prior to cyane oxidation evaluations.

Experiment 8

AuMgCrTiO $$AU_{0.00495} Mg_{0.0099} Cr_{0.00495} (TiO_{2-x}(OH)_{2x})_{0.98}$$

46.14 ml of ethanol (Quantum Chemical, 290, Newark, N.J., dehydrated punctilious) was combined with 20.214 ml of a 60 volume % solution in ethanol, containing titanium butoxide (Aldrich, 24, 411-2), under an inert nitrogen atmosphere. 0.818 ml of an 0.219 M aqueous solution containing AuCl$_3$ (Aldrich, 33, 404-9) (prepared using water and a 3:1 HCl:Au molar ratio of 37 wt % HCl, E.M. Sciences, Gibbstown, N.J.) was simultaneously added with 2.00 ml of 0.179 M aqueous magnesium citrate (Alfa, 39368), 0.119 ml of 1.5 M aqueous chromium hydroxide acetate, Cr$_3$(OH)$_2$(CH$_3$COO)$_7$ (Aldrich, 31, 810-8), and 0.709 ml of glacial acetic acid, (J. T. Baker, 6903-05, Phillipsburg, N.J.).

The aqueous solutions were simultaneously added to the alkoxide solution. The container was gently swirled during this addition. A cloudy green/white gelatinous material was produced. After aging for at least 24 hours in air, the material was dried at 120° C. in a vacuum oven, and subsequently calcined to 250° C. in air for five hours, prior to cyane oxidation evaluations.

Experiment 9

AuMgCrTiO

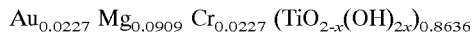
Au$_{0.0227}$ Mg$_{0.0909}$ Cr$_{0.0227}$ (TiO$_{2-x}$(OH)$_{2x}$)$_{0.8636}$ The same procedure and reagents were used as described for Experiment 8, with the following differences:

3.216 ml of AuCl$_3$ solution 15.243 ml of titanium n-butoxide solution 15.749 ml of magnesium citrate solution 0.469 ml of chromium hydroxide acetate solution 34.789 ml of ethanol 0.535 ml of glacial acetic acid A cloudy green/white gel was produced, and was treated in the same manner as described for Experiment 8.

Experiment 10

AuMgCrZrO

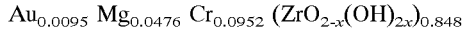
Au$_{0.0095}$ Mg$_{0.0476}$ Cr$_{0.0952}$ (ZrO$_{2-x}$(OH)$_{2x}$)$_{0.848}$ 1.836 ml of ethanol (Quantum Chemical, 290, Newark, N.J., dehydrated punctilious) was combined with 65.530 ml of a 0.558 M solution in ethanol containing zirconium n-propoxide (Alfa, 22989) under an inert nitrogen atmosphere 1.827 ml of an 0.2248 M aqueous solution containing AuCl$_3$ (Aldrich, 33, 404-9) was simultaneously added with 11.408 ml of 0.180 M aqueous magnesium citrate (Alfa, 39368), and 2.738 ml of 1.5 M aqueous chromium hydroxide acetate, Cr$_3$(OH)$_2$(CH$_3$COO)$_7$ (Aldrich, 31, 810-8). The aqueous solutions were simultaneously added to the alkonide solution. The container was gently swirled during this addition. A cloudy yellow/white gelatinous material was produced. After aging for at least 24 hours in air, the material was dried at 120° C. in a vacuum oven, and subsequently calcined to 250° C. in air for five hours, prior to cyane oxidation evaluations.

Experiment 11

AuMgCrAlO

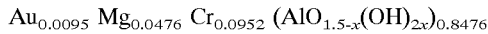
Au$_{0.0095}$ Mg$_{0.0476}$ Cr$_{0.0952}$ (AlO$_{1.5-x}$(OH)$_{2x}$)$_{0.8476}$ 69.574 ml of a 0.05 M solution, in ethanol, of aluminum isopropoxide (Aldrich, 22, 904-7) was added to the reactor container. In a second step, 0.525 ml of an 0.0744 M aqueous solution containing AuCl$_3$ (Aldrich, 33, 404-9) was simultaneously added with 1.086 ml of 0.180 M aqueous magnesium citrate (Alfa, 39368), 0.361 ml of 1.5 M aqueous chromium hydroxide acetate, Cr$_3$(OH)$_2$(CH$_3$COO)$_7$ (Aldrich, 31, 810-8). The aqueous solutions were simultaneously added to the alkoxide solution. The container was gently swirled during this addition. A cloudy, red colored gel was produced. After aging for at least 24 hours in air, the material was dried at 120° C. in a vacuum oven, and subsequently calcined to 250° C. in air for five hours, prior to cyane oxidation evaluations. This Experiment produced an aluminum based combination of hydroxides and oxides.

Experiment 12

AuMgCrAlO

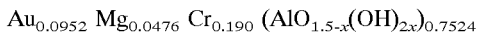
Au$_{0.0952}$ Mg$_{0.0476}$ Cr$_{0.190}$ (AlO$_{1.5-x}$(OH)$_{2x}$)$_{0.7524}$ The same procedure was used as in Experiment 11, except for the volume changes listed below. A cloudy, red colored gel was produced.

0.592 ml of AuCl$_3$ solution 69.552 ml of the aluminum isopropoxide solution 1.223 ml of the magnesium citrate solution 0.587 ml of the chromium hydroxide acetate solution

EXAMPLES

Reactions were run using 2 mL or 30 mL glass vials. The starting solution for all reactions was distilled cyclohexane, or spectral grade cyclohexane, containing a known wt % (approximately 1–2%) of CB (chlorobenzene) as an internal GC (gas chromatography) reference. All reaction products were first derivatized with BSTFA (bis(trimethylsilyl) trifluoroacetamide/1% trimethylchlorosilane, Supelco, Inc., Bellefornte, Pa.), a standard derivatizing agent before analysis by GC. The procedure for BSTFA derivatization consisted of adding 10 vol % BSTFA per volume of product to an aliquot of reaction product, stirring for 1 hr at 50° C. and cooling to room temperature. GC analyses were done using a 15 m DB-17 capillary column with a 0.32 mm internal diameter (J. & W. Scientific, Folsum, Calif.). The liquid phase of the column was comprised of 50 wt % (phenyl) methyl polysiloxane.

All reactions were heated for the times shown in Tables I–IV under Heating Time until the set temperature was reached. The reactions were held at this temperature for the times shown under Hold Time, then the contents were cooled and analyzed.

Results of reaction product GC analyses are shown in Tables I, II, III, and IV as % Conversion (% of cyclohexane converted to GC analyzable products), % Selectivity (% ratio of the sum of products K, A and CHHP divided by total sum of products), and as CHHP/K,A,CHHP) (product ratio of CHHP/(K+A+CHHP). All calculations are based on molarities of products as determined by GC. The molarity M of a given product compound was calculated from the equation:

$$M_{Compound} = \frac{area\%_{Compound} \times M_{CB} \times R.F._{Compound}}{area\%_{CB}}$$

R.F.$_{Compound}$(GC response factor for a given compound) was determined from calibration solutions containing known amounts of each product compound measured by GC and chlorobenzene from the equation:

$$R.F._{Compound} = \frac{M_{Compound} / area\%_{Compound}}{M_{CB} / area\%_{CB}}$$

% Conversion and % Selectivity were further defined by the equations:

$$\% \text{ Conversion} = \frac{100 \times \text{Sum of } M \text{ for all product compounds}}{M_{cyclohexane}(=9.29 M)}$$

$$\% \text{ Selectivity} = \frac{100 \times \text{Sum of } M \text{ for } (K + A + CHHP)}{\text{Sum of } M \text{ for all product compounds}}$$

Examples 1–22 and Comparative Examples A–L (Tables I and II) give results of cyclohexane oxidation experiments obtained using 2 mL glass vials. Each vial was charged with 0.5 or 1.0 mL of cyclohexane/CB solution and was pressurized to 500 psig with air. Vials were then heated at the temperatures shown and for the times indicated. Vials were stirred with Teflon® coated stir bars.

Examples 23–28 and Comparative Examples M–S (Tables III and IV) give results of cyclohexane oxidation experiments obtained using 30 mL glass vials. Each vial was charged with 5.0 mL of cyclohexane/CB solution and was pressurized to 500 psig with air. Vials were then heated at the temperatures shown and for the times indicated, and were agitated. Some examples involve the use of an initiator (propionaldehyde).

TABLE I

| Ex. | Catalyst, g. | Prep Method | Sol., mL | Reaction Temp., °C. | Heating Time, min. | Hold Time, min. | Conv., % | Select., % | CHHP/ K,A,CHHP |
|---|---|---|---|---|---|---|---|---|---|
| 1 | Au/Al$_2$O$_3$, 0.0202 | Exp. 1 | 0.5 | 160 | 36 | 9 | 1.85 | 97.4 | 0.03 |
| 2 | Au/Al$_2$O$_3$, 0.0201 | Exp. 1 | 1.0 | 160 | 36 | 144 | 2.82 | 96.6 | 0 |
| 3 | Au/Al$_2$O$_3$, 0.0204 | Exp. 1 | 1.0 | 170 | 39 | 1 | 1.79 | 96.4 | 0.01 |
| 4 | Au/Al$_2$O$_3$, 0.0203 | Exp. 1 | 1.0 | 170 | 39 | 7 | 1.90 | 95.7 | 0 |
| 5 | Au/Al$_2$O$_3$, 0.0206 | Exp. 1 | 0.5 | 170 | 39 | 7 | 4.28 | 93.9 | 0.01 |
| 6 | Au/Al$_2$O$_3$, 0.0200 | Exp. 1 | 0.5 | 170 | 39 | 7 | 4.31 | 93.8 | 0.01 |
| 7 | Au/Al$_2$O$_3$, 0.0113 | Exp. 1 | 1.0 | 190 | 45 | 2 | 2.06 | 91.6 | 0 |
| 8 | Au/Al$_2$O$_3$, 0.0106 | Exp. 1 | 1.0 | 190 | 45 | 10 | 2.30 | 90.8 | 0 |
| 9 | CrZrO, 0.0202 | Exp. 2 | 0.5 | 160 | 36 | 9 | 0.68 | — | 0.09 |
| 10 | CrZrO, 0.0201 | Exp. 2a | 0.5 | 170 | 39 | 7 | 4.77 | 86.2 | 0.0 |
| 11 | CrTaO, 0.0202 | Exp. 3 | 0.5 | 160 | 36 | 9 | 1.97 | 98.1 | 0.11 |
| 12 | CrTaO, 0.0210 | Exp. 3a | 0.5 | 170 | 39 | 7 | 3.91 | 87.2 | 0.01 |
| 13 | CrTiO, 0.0196 | Exp. 4 | 0.5 | 160 | 36 | 9 | 3.53 | 96.8 | 0.03 |
| 14 | CrTiO, 0.0215 | Exp. 4 | 0.5 | 170 | 39 | 7 | 3.85 | 89.6 | 0 |
| 15 | CoSiTiO, 0.0206 | Exp. 7 | 0.5 | 160 | 36 | 9 | 3.75 | 97.8 | 0 |
| 16 | CoCrTiO, 0.0209 | Exp. 5 | 0.5 | 160 | 36 | 9 | 3.92 | 94.7 | 0 |
| 17 | CoCrTiO, 0.0202 | Exp. 5 | 0.5 | 170 | 39 | 7 | 3.73 | 93.1 | 0 |
| 18 | TiSiO, 0.0209 | Exp. 6 | 0.5 | 160 | 36 | 9 | 0 | — | — |
| 19 | AuMgCrTiO, 0.0106 | Exp. 9 | 0.5 | 170 | 39 | 6 | 4.10 | 91.6 | 0.19 |
| 20 | AuMgCrZrO, 0.0208 | Exp. 10 | 0.5 | 170 | 39 | 6 | 4.91 | 92.3 | 0 |
| 21 | AuMgCrAlO, 0.0202 | Exp. 11 | 0.5 | 170 | 39 | 6 | 2.94 | 98.9 | 0 |
| 22 | AuMgCrAlO, 0.0205 | Exp. 12 | 0.5 | 170 | 39 | 6 | 3.22 | 98.6 | 0 |

TABLE II

| Comp. Ex. | Catalyst | Sol., mL | Reaction Temp., °C. | Heating Time, Min. | Hold Time, min. | Conv., % | Select., %. | CHHP/ K,A,CHHP |
|---|---|---|---|---|---|---|---|---|
| A | No catalyst | 0.5 | 160 | 36 | 9 | 7.81 | 85.6 | 0.21 |
| B | No catalyst | 0.5 | 160 | 36 | 9 | 7.67 | 87.5 | 0.11 |
| C | No catalyst | 0.5 | 160 | 36 | 9 | 4.24 | 97.2 | 0.51 |
| D | No catalyst | 1.0 | 160 | 36 | 9 | 4.60 | 96.4 | 0.51 |
| E | No catalyst | 1.0 | 160 | 36 | 144 | 4.21 | 85.8 | 0.02 |
| F | No catalyst | 1.0 | 170 | 39 | 7 | 2.98 | 85.6 | 0.01 |
| G | No catalyst | 1.0 | 170 | 39 | 7 | 3.19 | 85.5 | 0.05 |
| H | No catalyst | 0.5 | 170 | 39 | 7 | 5.27 | 83.2 | 0.01 |
| I | No catalyst | 0.5 | 170 | 39 | 7 | 5.81 | 83.1 | 0.02 |
| J | No catalyst | 0.5 | 170 | 39 | 7 | 6.23 | 78.3 | 0.02 |
| K | No catalyst | 1.0 | 190 | 45 | 2 | 2.50 | 84.9 | 0 |
| L | No catalyst | 1.0 | 190 | 45 | 10 | 2.40 | 84.8 | 0 |

TABLE III

| Ex. | Catalyst, g. | Prep Method | Sol., mL | Reaction Temp., °C. | Heating Time, Min. | Hold Time, min. | Conv., % | Select., %. | CCHP/ K,A, CHHP | % Propion- aldehyde |
|---|---|---|---|---|---|---|---|---|---|---|
| 23 | Au/Al$_2$O$_3$, 0.0501 | Exp. 1 | 5.0 | 170 | 15 | 30 | 7.00 | 79.6 | 0 | 0.5 |
| 24 | Au/Al$_2$O$_3$, 0.0527 | Exp. 1 | 5.0 | 170 | 15 | 30 | 6.82 | 83.8 | 0 | 0.5 |
| 25 | Au/Al$_2$O$_3$, 0.0518 | Exp. 1 | 5.0 | 170 | 15 | 30 | 2.72 | 97.2 | 0 | 0.3 |
| 26 | Au/Al$_2$O$_3$, 0.0550 | Exp. 1 | 5.0 | 170 | 15 | 30 | 3.48 | 96.3 | 0 | 0.1 |
| 27 | Au/Al$_2$O$_3$, 0.0511 | Exp. 1 | 5.0 | 170 | 45 | 30 | 4.63 | 96.0 | 0.19 | 0 |
| 28 | AuMgCrTiO, 0.0507 | Exp. 8 | 5 | 170 | 45 | 30 | 4.81 | 89.7 | 0.08 | 0 |

TABLE IV

| Comp. Ex. | Catalyst, g | Sol., mL | Reaction Temp., °C. | Heating Time, Min. | Hold Time, min. | Conv., % | Select., %. | CHHP/ K,A,CHHP | % Propion- aldehyde |
|---|---|---|---|---|---|---|---|---|---|
| M | No catalyst | 5.0 | 170 | 15 | 30 | 4.38 | 85.4 | 0.08 | 0.1 |
| N | No catalyst | 5.0 | 170 | 15 | 30 | 7.51 | 69.4 | 0.05 | 0.5 |
| O | No catalyst | 5.0 | 170 | 15 | 30 | 7.45 | 69.3 | 0.03 | 0.5 |
| P | No catalyst | 5.0 | 170 | 15 | 30 | 4.46 | 83.8 | 0.10 | 0 |
| Q | No catalyst | 5.0 | 170 | 45 | 30 | 6.56 | 81.5 | 0.04 | 0 |
| R | No catalyst | 5.0 | 170 | 45 | 30 | 7.21 | 81.2 | 0.07 | 0 |
| S | No catalyst | 5.0 | 170 | 45 | 30 | 6.39 | 82.3 | 0.05 | 0 |

Although particular embodiments of the present invention have been described in the foregoing description, it will be understood by those skilled in the art that the invention is capable of numerous modifications, substitutions and rearrangements without departing from the spirit or essential attributes of the invention. Reference should be made to the appended claims, rather than to the foregoing specification, as indicating the scope of the invention.

We claim:

1. An improved process for oxidizing a cycloalkane in a reaction mixture to form a product mixture containing a corresponding alcohol and ketone, the improvement comprising:
    contacting the reaction mixture with a source of oxygen and a catalytic amount of a heterogenous catalyst selected from the group consisting of (1) gold, (2) a sol-gel compound of gold, and (3) a sol-gel compound comprised of (a) one or more members selected from a first group consisting of Cr, Co and Ti and (b) one or more members selected from a second group consisting of Zr, Ta, Nb, Si, Mg, Al and Ti with the proviso that hydrogen is not present in the reaction mixture if the catalyst is gold supported on titania or sol-gel compound of gold supported on titania, that the selected members of (b) are combined with an oxide, and that members of group (a) cannot be the same as the members of group (b).

2. The process according to claim 1 wherein the cycloalkane is cyclohexane.

3. The process according to claim 2 wherein the corresponding alcohol is cyclohexanol and the corresponding ketone is cyclohexanone.

4. The process according to claim 1 wherein the heterogenous catalyst is supported on a catalyst support member.

5. The process according to claim 4 wherein the catalyst support member is Al$_2$O$_3$.

6. The process according to claims 4 or 5 wherein the catalyst is gold and wherein the gold is present on the support member as well-dispersed particles having a diameter from about 3 nm to about 15 nm.

7. The process according to claim 1 wherein the reaction temperature is from about about 160° C. to about 200° C., and reaction pressure is from about 69 kPa to about 2760 kPa.

8. The process according to claim 7 wherein the reaction temperature is from about 160° C. to about 180° C.

9. The process according to claim 1 wherein the source of oxygen is air.

10. The process according to claim 6 wherein the gold is from about 0.1 to about 10 wt. percent of the catalyst and support member.

11. The process according to claim 1 wherein an initiator is also present with the catalyst.

12. The process according to claim 11 wherein the initiator is propionaldehyde.

13. The process according to claim 1 wherein the sol-gel compound contains Cr and/or Co.

14. The process according to claim 1 wherein the oxide is an inorganic matrix of hydroxides or oxides, or combinations thereof.

15. The process according to claim 14 where the inorganic matrix is an aluminum based combination of hydroxides and oxides.

16. The process according to claim 1 wherein the gold catalyst is in the form of a sol-gel compound.

17. The process according to claim 1 wherein the gold catalyst is in the form of a sol-gel compound comprising Au and Cr.

* * * * *